United States Patent
Löffler et al.

(10) Patent No.: US 11,266,462 B2
(45) Date of Patent: Mar. 8, 2022

(54) MEDICAL INSTRUMENT FOR TISSUE ABLATION BY MEANS OF AN HF ELECTRODE WITH THE FUNCTION OF A CONTROLLED DISTAL ANGULAR ORIENTATION

(71) Applicant: Karl Storz SE & Co. KG, Tuttlingen (DE)

(72) Inventors: Oliver Löffler, Boll (DE); Stefan Rehbein, Immendigen-Hattingen (DE); Uwe Wittke, Tuttlingen-Möhringen (DE); Frank Doll, Talheim (DE); Rainer Hermle, Gosheim (DE); Udo Nagele, Wörgl (AT)

(73) Assignee: KARL STORZ SE & CO. KG, Tuttlingen (DE)

( * ) Notice: Subject to any disclaimer, the term of this patent is extended or adjusted under 35 U.S.C. 154(b) by 408 days.

(21) Appl. No.: 16/117,187

(22) Filed: Aug. 30, 2018

(65) Prior Publication Data

US 2019/0069946 A1 Mar. 7, 2019

(30) Foreign Application Priority Data

Sep. 5, 2017 (DE) ..................... 10 2017 120 341.9

(51) Int. Cl.
*A61B 18/14* (2006.01)
*A61B 18/12* (2006.01)
(Continued)

(52) U.S. Cl.
CPC .......... *A61B 18/14* (2013.01); *A61B 18/1206* (2013.01); *A61B 18/1485* (2013.01);
(Continued)

(58) Field of Classification Search
CPC ...... A61B 2018/141; A61B 2018/1407; A61B 2018/2905; A61B 18/082; A61B 18/14;
(Continued)

(56) References Cited

U.S. PATENT DOCUMENTS 5,976,129 A 11/1999 Desai
6,203,525 B1 * 3/2001 Whayne ............. A61B 18/1492
604/95.01
(Continued)

FOREIGN PATENT DOCUMENTS

DE 10354830 A1 6/2004
EP 1 974 683 A1 10/2008

OTHER PUBLICATIONS

ASM Material Data Sheet, 2003, ASM Aerospace Specification Metals Inc. (Year: 2003).*
(Continued)

*Primary Examiner* — Linda C Dvorak
*Assistant Examiner* — Nicholas S Borsch
(74) *Attorney, Agent, or Firm* — Eversheds Sutherland (US) LLP

(57) ABSTRACT

The disclosure relates to a medical instrument for minimally invasive tissue ablation by means of an HF electrode, with a hollow shaft, wherein the HF electrode is electrically insulated from the hollow shaft, is arranged at a distal end of the latter and, in order to ablate tissue, protrudes axially beyond the hollow shaft at least in part. The angle orientation of the HF electrode relative to the hollow shaft is adjustable in a controlled manner to a working position in which the HF electrode, protrudes radially beyond an outer circumference of the hollow shaft in order to ablate tissue. In the working position, by means of suitable adjustment of the shaft and of the HF electrode, a position can always be found in which the distal end of the HF electrode sufficiently (Continued)

reaches or touches tissue portions that are to be ablated in the region of the bladder neck.

14 Claims, 7 Drawing Sheets

(51) Int. Cl.
  *A61B 18/00* (2006.01)
  *A61B 1/307* (2006.01)
  *A61B 17/00* (2006.01)
(52) U.S. Cl.
  CPC ............ *A61B 1/307* (2013.01); *A61B 18/149* (2013.01); *A61B 2017/00274* (2013.01); *A61B 2018/00196* (2013.01); *A61B 2018/00517* (2013.01); *A61B 2018/00547* (2013.01); *A61B 2018/00577* (2013.01); *A61B 2018/00601* (2013.01); *A61B 2018/126* (2013.01); *A61B 2018/1407* (2013.01); *A61B 2018/1475* (2013.01)
(58) Field of Classification Search
  CPC .. A61B 2018/00601; A61B 2018/1475; A61B 2018/00196; A61B 18/149; A61B 17/221; A61B 17/32056; A61B 2017/00862; A61B 2017/00867; A61B 2017/00871; A61B 2018/00059; A61B 2018/00071; A61B 2018/00077; A61B 2018/00083; A61B 18/12; A61B 18/1206; A61B 2018/1233; A61B 2018/1256; A61B 2018/126; A61B 2018/128
  USPC ...................................................... 606/46, 41
  See application file for complete search history.

(56) References Cited

U.S. PATENT DOCUMENTS

| | | |
|---|---|---|
| 6,231,591 B1 | 5/2001 | Desai |
| 6,451,014 B1 | 12/2002 | Wakikaido et al. |
| 7,704,249 B2 * | 4/2010 | Woloszko ............ A61B 18/149 606/48 |
| 2005/0038424 A1 * | 2/2005 | Okada .................... A61B 18/14 606/47 |
| 2005/0251134 A1 | 11/2005 | Wooszko et al. |

OTHER PUBLICATIONS

ASM Material Data Sheet proof of date (Year: 2021).*
Material Data Sheet, Jan. 31, 2016, Nitinol Devices and Components (Year: 2016).*
Material Data Sheet proof of date (Year: 2021).*
Search Report, EP 18185937.2, dated Feb. 11, 2019 (in German) (7 pgs.).
Search Report, DE 10 2017 120 341.9, dated Apr. 12, 2018 (7 pgs.).

* cited by examiner

MEDICAL INSTRUMENT FOR TISSUE ABLATION BY MEANS OF AN HF ELECTRODE WITH THE FUNCTION OF A CONTROLLED DISTAL ANGULAR ORIENTATION

FIELD OF THE INVENTION

The invention relates to a medical instrument for minimally invasive surgery, in particular a medical instrument, preferably a resectoscope, for tissue ablation by means of an HF electrode with the function of a controlled angle orientation of the distal instrument region.

BACKGROUND OF THE INVENTION

It is nowadays no longer possible to imagine modern medicine without minimally invasive surgery. For minimally invasive surgery of the bladder or prostate, transurethral resection (TUR) is used as a urological or gynecological operating technique for the ablation of diseased tissue. The operation is performed endoscopically through the urethra without an external incision. An HF electrode is inserted into the bladder, and a high-frequency alternating current is applied to the electrode in order to ablate harmful or damaged tissue.

Conventional resectoscopes have at least a hollow shaft and are of a stiff configuration in order to make them easier to fit in place and at the same time to afford good guidance for the HF electrode. In bladder resection procedures, in which among other things harmful tissue is removed from the bladder, the tissue to be ablated may be located in the interior of the bladder and, to be more exact, at a lateral distance from the urinary canal, i.e. posterior to the bladder neck. Although in this case the resectoscope can indeed be inserted through the urinary canal, it cannot be guided directly to the operating site located laterally with respect to the insertion axis. This is at best possible, to a limited extent, by traumatic leverage or tilting of the resectoscope.

DE 2006 039 696 A1 discloses a device for resection and/or ablation of organic tissue by means of HF currents. The device comprises an HF coil and a corresponding shaft-shaped support. The coil can be subjected to HF currents such that cutting can be carried out with a wedge-shaped HF cutting edge in order to perform an electrochemical HF operation. However, the HF cutting edge is usable only along a mid-line of the instrument. Bending or angling of the HF cutting edge is not possible.

EP 2 298 204 B1 from the applicant likewise discloses a medical instrument for bipolar electrosurgery, with a (stiff) outer shaft, at the distal end of which a cutting edge is arranged which can be subjected to HF currents and at the same time is insulated from the outer shaft. With this device, however, cutting is again possible only along the mid-line of the shaft. Bending of the HF cutting edge is not possible.

DISCLOSURE OF THE INVENTION

It is therefore an object of the present invention to make available a medical instrument for minimally invasive tissue ablation by means of an HF electrode, which medical instrument can be used even more flexibly in order to specifically ablate tissue particularly even at regions that are usually difficult to access, particularly in applications in transurethral resection.

According to the invention, this object is achieved by the medical instrument according to claim 1. Further advantageous embodiments are set out in the subclaims.

According to the present invention, a medical instrument for minimally invasive tissue ablation by means of an HF electrode is made available which has a hollow shaft, wherein the HF electrode is electrically insulated from the hollow shaft, is arranged at a distal end of the latter and, in order to ablate tissue, protrudes axially beyond the hollow shaft at least in part. According to the invention, the angle orientation of the HF electrode relative to the hollow shaft is adjustable in a controlled manner to a working position in which the HF electrode, seen in a front view of the hollow shaft, protrudes radially beyond an outer circumference of the hollow shaft in order to ablate tissue.

On the basis of this angle adjustment, the shaft of the instrument can be inserted through an opening into the body of a patient, in particular through a urethra, and arranged in the operating region without any danger of causing damage to the HF electrode or tissue. The angle position of the HF electrode can then be suitably adjusted such that tissue regions at a distance from the insertion axis are then easily reachable for tissue ablation.

According to a further embodiment, the HF electrode has an electrical insulation channel and an HF coil, wherein the insulation channel electrically insulates the HF electrode from the hollow shaft and protrudes axially beyond the distal end of the shaft in order to ablate tissue, and wherein a distal end of the HF coil protrudes axially beyond the distal end of the insulation channel in order to ablate tissue.

According to a further embodiment, the distal end of the HF coil is formed by an ablation edge which merges, via a symmetrically curved ablation edge, into a connection portion for applying a high-frequency voltage to the HF coil, wherein the angle orientation of the connection portion relative to a mid-line of the hollow shaft is adjustable in a controlled manner in order to adjust in a controlled manner the angle orientation of the HF coil relative to the hollow shaft.

In an insertion position, the distal end of the HF coil protrudes particularly in a hook shape from supply lines of the HF electrode, in particular at an angle of 60 to 180°, for example in the region of or exactly 90 degrees. Even small angle adjustments of the HF electrode can then result in a comparatively large change of the distance of the distal end of the HF coil from the mid-line of the shaft of the medical instrument.

According to a further embodiment, the connection portion is made of a flexible or elastic, electrically conductive material. The angle orientation of the HF coil relative to the hollow shaft can thus in an advantageously simple way be adjusted in a controlled manner by bending or kinking of the connection portion. For this purpose, in particular the material strength or the diameter of the aforementioned connection portion, the material being the same otherwise, can be reduced by comparison with the other portions of the HF electrode.

According to a further embodiment, the HF electrode is preferably elastically prestressed to the working position. The HF electrode can thus be loaded to a greater extent and yields less upon contact with the tissue portions that are to be ablated, which results in greater positioning precision of the HF electrode. In the working position, a distal end of the connection portion is bent or kinked relative to a proximal end of the connection portion in order to enclose a suitable acute angle with the mid-line of the hollow shaft.

According to a further embodiment, the HF electrode is guided longitudinally displaceably with respect to the hollow shaft, wherein, by adjustment of the HF electrode toward the proximal end of the hollow shaft, the HF electrode can be adjusted to an insertion position in which the distal end of the connection portion is substantially flush with the proximal end of the connection portion, and the HF coil preferably does not protrude beyond an inner profile formed by inner faces of the hollow shaft, so as to reduce the danger of damage to tissue or to the HF electrode. Preferably, during an axial adjustment of the HF electrode, the angle position of the latter is also automatically modified. More preferably, the angle of inclination of the HF electrode relative to the mid-line of the shaft is automatically changed increasingly as the axial adjustment increases. Thus, through the choice of the axial adjustment, the angle position of the HF electrode can also be precisely set, which permits advantageously simple positioning.

According to a further embodiment, the connection portion is for this purpose guided longitudinally displaceably relative to the electrical insulation channel, or the electrical insulation channel is guided longitudinally displaceably relative to the hollow shaft, which can make the construction of the medical instrument advantageously straightforward.

According to a further embodiment, the connection portion is guided longitudinally displaceably in a cover tube which is arcuately curved relative to the mid-line of the hollow shaft or can be arcuately curved by suitable adjustment, such that the position and angle orientation of the HF coil relative to the hollow shaft is adjustable in a controlled manner by a simple longitudinal adjustment of the HF electrode in order to bend or kink the connection portion.

According to a further embodiment, the cover tube is formed directly as a portion of the insulation channel.

According to a further embodiment, the cover tube is alternatively configured as a hollow pulling or pushing rod, which is coupled to the HF electrode. By mechanical adjustment of the pulling or pushing rod, it is thus possible to precisely position the HF electrode in an advantageously simple manner.

According to a further embodiment, the cover tube is alternatively formed from a memory material, of which the rest position with respect to the mid-line of the hollow shaft is rectilinear or angled, wherein the orientation of a distal end of the cover tube relative to the mid-line of the hollow shaft is adjustable, in particular by application of an electric current or by a temperature change. By changing simple physical parameters, it is thus possible for the HF electrode to be positioned in a precise and reproducible manner.

According to a further embodiment, a deflection element is provided at the distal end of the hollow shaft, on which deflection element the connection portion or the electrical insulation channel bears directly, wherein the deflection element is configured in such a way that longitudinal displacement of the HF electrode with respect to the hollow shaft causes an increasing bending or kinking of the connection portion or of the electrical insulation channel. For this purpose, the deflection element is expediently arranged less far from the mid-line of the hollow shaft than the supply lines of the HF electrode. With increasing distal adjustment of the HF electrode, and on account of the supply lines bearing on the deflection element, the HF electrode thus moves away more and more from the mid-line, in particular by bending or kinking of the aforementioned connection portion.

According to a further embodiment, an adjustable angling element is moreover provided, wherein the angle orientation of the HF coil relative to the hollow shaft is adjustable in a controlled manner by adjustment of the angling element in contact with a portion of the HF electrode or of the electrical insulation channel. For this purpose, the angling element can be mechanically adjustable by a pulling device, a rod or the like.

According to a further embodiment, the angling element has a piezoelectric element or a thermally adjustable element, such that the angle position of the HF electrode can be precisely adjusted by a simple modification of physical parameters.

According to a further embodiment, the HF electrode has hinges which are arranged on the connection portion, such that the angle orientation of the HF coil relative to the hollow shaft is adjustable in a controlled manner by adjustment of the hinges, in particular by kinking of the hinges. This can permit overall a greater stiffness of the HF electrode and less yield thereof upon contact with tissue that is to be ablated, in particular because connection or supply portions of the HF electrode do not have to be configured with smaller material thickness. For this purpose, the hinges can in particular be assigned elastic restoring means in order to elastically prestress the HF coil to a rectilinear or angled rest position.

According to a further embodiment, an advantageously simple, precise and reproducible adjustment of the angle orientation of the HF electrode can be achieved by the fact that the HF electrode is formed at least in part from a memory metal, which is configured such that the angle orientation of the HF coil relative to the hollow shaft is adjustable in a controlled manner, in particular by application of an electric current or by a temperature change.

According to a further embodiment, the hollow shaft has a hollow outer shaft and an inner shaft received therein, wherein the inner shaft is guided longitudinally displaceably in the hollow outer shaft, and wherein the HF electrode can be retracted completely into the hollow outer shaft. Through the longitudinal displaceability of the inner shaft relative to the outer shaft, the adjustment range of the HF electrode can thus be further increased.

According to a further embodiment, an angle of inclination of the HF electrode relative to the mid-line of the hollow shaft can be adjusted by an angle of up to 90°. This adjustment angle more preferably lies in a range from 50° to 75°, which corresponds to the typical opening angle of the human bladder in the region of the bladder neck. The maximum (minimum) adjustment angle is expediently slightly greater than the typical maximum (minimum) opening angle of the human bladder in the region of the bladder neck. To permit a reliable limitation of this angle adjustment range, mechanical angle stops or the like can be provided.

OVERVIEW OF THE FIGURES

Preferred embodiments according to the invention are described in more detail below with reference to the attached drawings, from which description further features, advantages and problems to be solved will become clear. In the drawings.

Figure 5A:
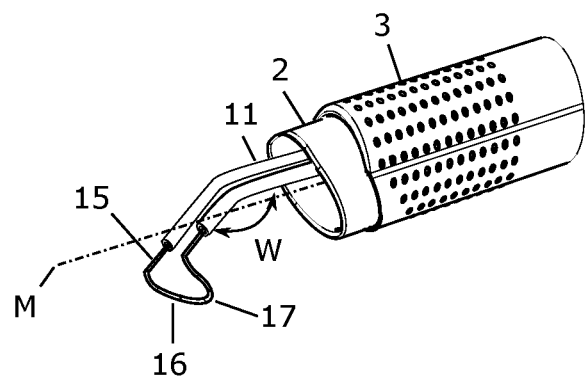
FIG. 5a shows a schematic perspective view of the distal region of the medical instrument according to a further embodiment of the present invention, with a distally arranged HF electrode whose angle position is adjustable by bending or angling of an electrical insulation channel.
Figure 5B:
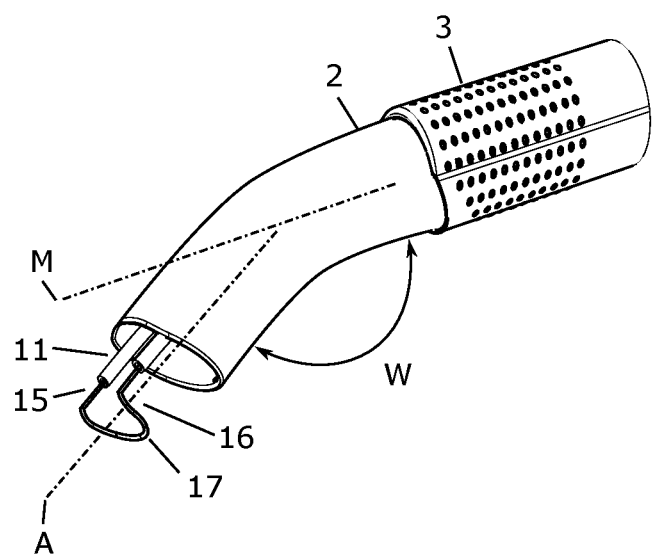
Figure 6:
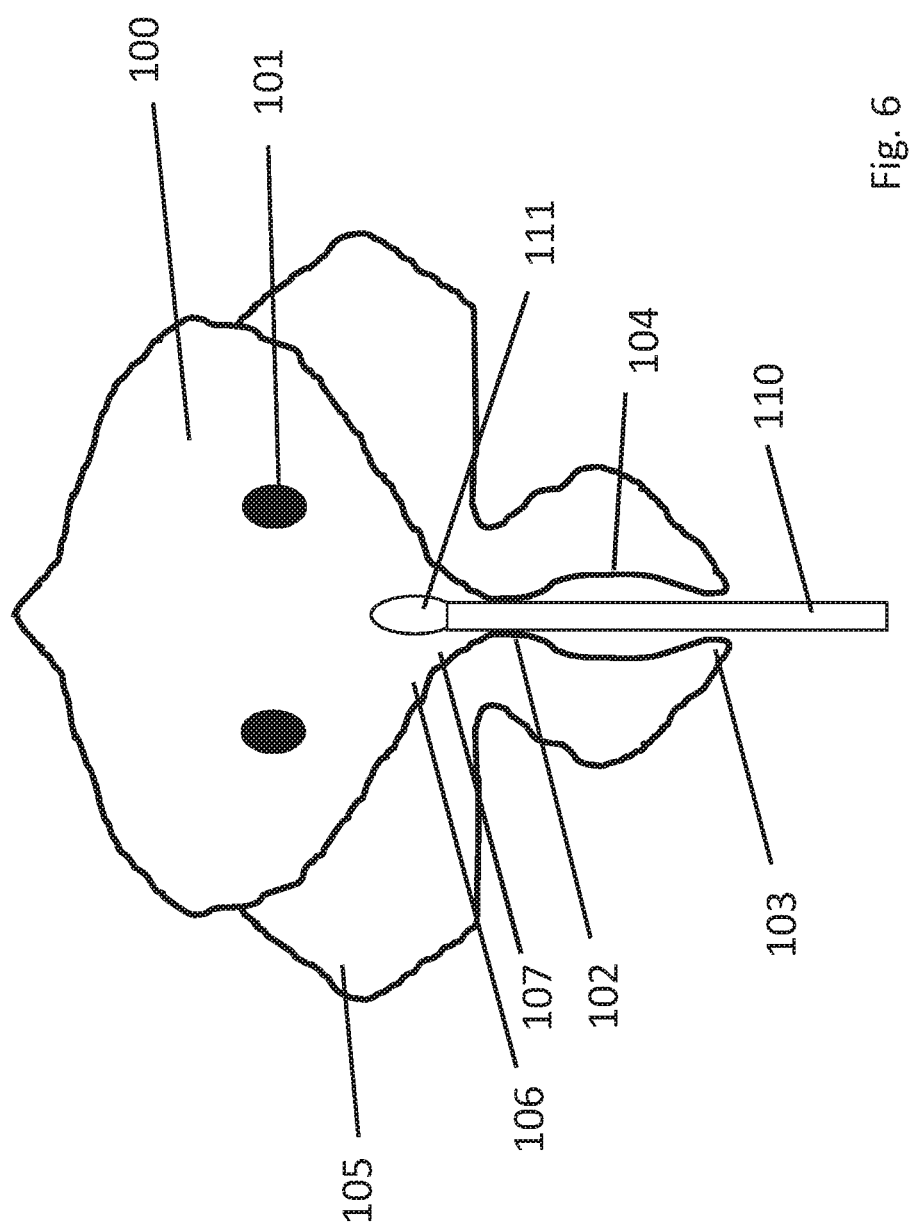

FIG. 5b shows a schematic perspective view of the distal region of the medical instrument according to a further embodiment of the present invention, with a distally arranged HF electrode whose angle position is adjustable by bending or angling of a distal portion of an inner shaft; and FIG. 6 shows the geometric relationships in a minimally invasive procedure performed on the bladder of a human patient, for further illustration of the advantages according to the present invention.

In the figures, identical reference signs designate identical or substantially equivalent elements or groups of elements.

DETAILED DESCRIPTION OF ILLUSTRATIVE EMBODIMENTS

In respect of the explanation of the terms used, it will be noted at this point that "distal" is to be understood in the sense of "toward the operating site" or "away from the operator" and is used synonymously with "forward". The word "proximal" is to be understood as the opposite of this, i.e. in the sense of "toward the operator" or "away from the operating site" and is used synonymously with "rearward".

First of all, FIG. 6 sets out the geometric relationships in minimally invasive procedures performed on the hollow organ formed by the human bladder 100. The ureters lead in pairs in the regions 101 into the bladder 100. The trigonum vesicae 106 is the triangular surface formed by points of entry of the two ureters and by the point of exit of the urethra. This innermost layer of the bladder is also called the mucosa 105. The shaft 110 of a medical instrument can be inserted through the urethra and the region of the outer sphincter muscle 103 and of the inner sphincter muscle 102 into the bladder 100 and in the process also passes the region of the prostate 104. With an HF electrode 111 conventionally located at the distal end of the shaft 110, access is therefore usually only possible to regions near an insertion axis, which is substantially defined by the two sphincter muscle regions 102, 103 and the urethra. However, if a tumor or damaged tissue is located remote from this insertion axis, minimally invasive procedures are usually possible only to a limited extent. A tilting of the shaft 110, even by only small angles, leads directly to damage of healthy tissue and is also extremely traumatic.

As is explained below, a medical instrument according to the present invention allows minimally invasive procedures to be performed specifically even laterally with respect to the aforementioned insertion axis, particularly in the region of the prostate 104 and in the region of the bladder neck 107, which usually has an opening angle in the range from approximately 50° to approximately 75°. As can be seen from FIG. 6, tissue portions on the inner wall of the bladder in the region of the bladder neck 107 are not located too far laterally from the aforementioned insertion axis. In order to purposefully ablate tissue portions specifically in this region by means of an HF electrode 111, the angle orientation of the HF electrode 111 relative to the shaft 110 can be adjusted in a controlled manner according to the invention to a working position in which the HF electrode 111, seen in a front view of the shaft 110, protrudes radially beyond an outer circumference of the shaft 110. In this working position, and by means of longitudinal adjustment of the shaft 110, i.e. by displacement along the aforementioned insertion axis, a position can always be found in which the distal end of the HF electrode 111 sufficiently reaches or touches tissue portions that are to be ablated in the region of the bladder neck 107. In order to reach tissue portions in other regions of the bladder neck 107, the shaft 110 only has to be adjusted axially along the aforementioned insertion axis and/or the angle of inclination of the HF electrode 111 relative to the shaft 110 or the aforementioned insertion axis simply has to be further adjusted. In other words, by suitably deep insertion of the shaft 110 and/or adjustment of the angle orientation of the HF electrode, all tissue portions in the region of the bladder neck 107 can be reached according to the invention.

As can be readily seen from FIG. 6, this also applies accordingly to tissue portions in the region of the prostate 104 that are situated laterally with respect to the aforementioned insertion axis.

Figure 1:
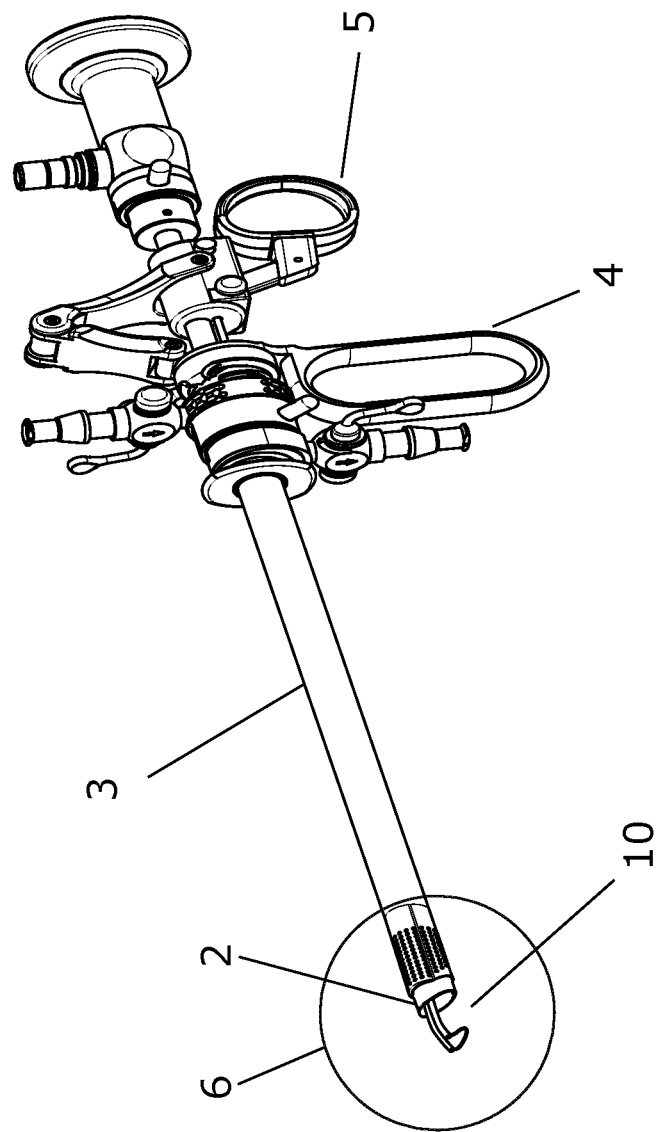
FIG. 1 shows a schematic perspective view of the whole medical instrument according to a preferred embodiment of the present invention.

FIG. 1 shows a medical instrument 1 serving as a basis for the embodiments of the present invention for ablation of tissue, in particular tissue in the region of the bladder neck or prostate, by a minimally invasive surgerical procedure. The medical instrument has basically three portions: a front or else distal portion 6, a control portion 5 located at a rear or proximal end, and a portion which is formed by the shaft 3, extends between the aforementioned portions and is connected to each of these.

The distal end 6 is located at the front end of the shaft 3 and comprises in particular a front opening from which there protrudes an HF electrode 10, which serves for tissue ablation by application of a high-frequency alternating current in the customary manner.

The shaft 3 has a substantially cylindrical shape and is of a suitable length and size to be inserted into a human body. In an alternative configuration, the shaft can also have an oval shape or other tube shape. In a minimally invasive surgical procedure, the shaft 3 can be used to insert operating instruments into the human body to the site of an operation.

The control portion has substantially two sub-portions, namely a positioning handle portion and an operating handle portion, which are connected to each other in a longitudinally movable manner via a transmission shank, for transmission of a force, and a positioning hinge, for the positioning and guiding of the shaft.

At the distal end of the control portion, a positioning handle 4 is in particular arranged which can be rigidly connected to the outer part of the shaft 3. In this way, the positioning handle 4 can be used to insert the medical instrument 1 into the human body and to position it at the operating site.

An eyepiece and an operating handle 5 are arranged on the operating handle portion at the proximal end of the control portion. The operator (i.e. the surgeon) is now able to guide his thumb through the operating handle 5 and the other fingers of one hand through the positioning handle 4 in order, by opening and closing his hand, to execute a forward and rearward movement of an inner shaft 2 relative to the hollow outer shaft of the shaft 3, such that the operator is able to operate with just one hand.

With the aid of the operating handle 5, parts of the medical instrument 1 can additionally be rotated. In particular, the rotation of an inner shaft relative to an outer shaft of the shaft 3 is possible.

Consequently, the medical instrument 1 according to this embodiment is thus a resectoscope with an inner shaft 2, at the distal end of which an HF electrode 10 is arranged for tissue ablation by application of high-frequency alternating currents.

It will be noted at this point that not all of the constituent parts of the above illustrative embodiment are necessary for the present invention. In particular, the proximal portion of the medical instrument 1 can also be configured differently than is shown in FIG. 1. Although the illustrative embodiment displays two shafts, namely an inner shaft 2 and an outer shaft 3, the basic configuration of the present invention requires only one shaft. According to the invention, the angle orientation of the HF electrode 10 relative to the inner shaft 2 and to the outer shaft 3 can be adjusted in a controlled manner, as is explained below.

Figure 2:
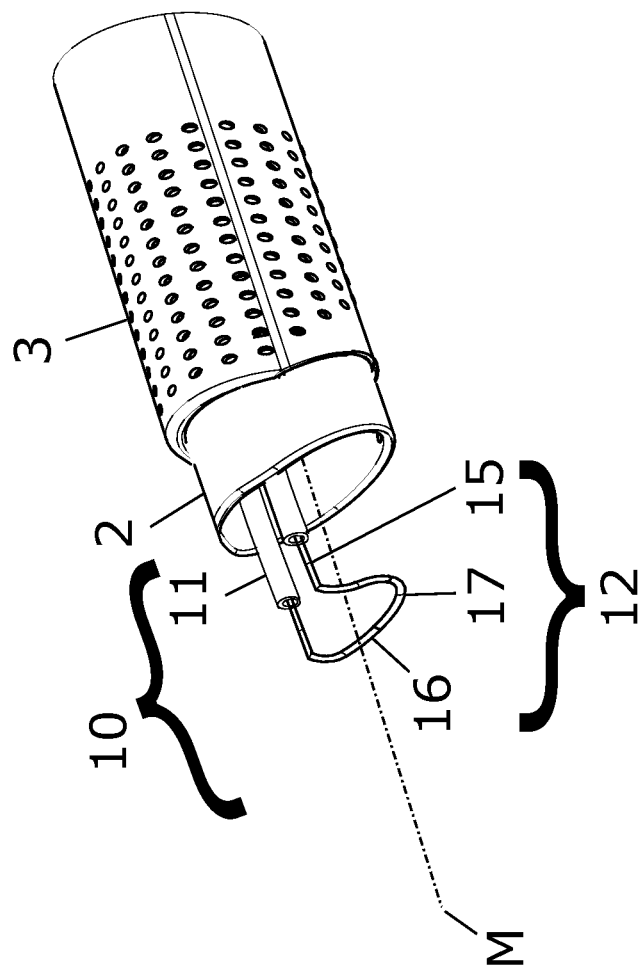
FIG. 2 shows an enlarged perspective view of the distal region of the medical instrument according to a preferred embodiment of the present invention, with an HF electrode which is adjustable in terms of its angle orientation and is (as yet) in a non-angled state.

FIG. 2 shows a detailed view of the distal portion 6 of the medical instrument 1 according to FIG. 1. Specifically, FIG. 2 shows the distal portions of the inner shaft 2 and of the outer shaft 3, wherein the distal end of the inner shaft 2 protrudes axially beyond the opening of the outer shaft 3. As has already been mentioned above, the inner shaft 2 can be guided longitudinally displaceably in the outer shaft 3. According to FIG. 2, the outer shaft 3 and the inner shaft 2 are each oriented parallel to the mid-line M which is used below as a reference line for the angle orientation of the HF electrode 10.

At its distal end, the outer shaft 3 has a multiplicity of orifice holes, which are distributed on the outer wall of the outer shaft 3. A rinsing liquid can be returned through the orifice holes.

The HF electrode 10 has an HF coil 12 and an insulation channel 11, wherein the HF coil 12 is guided in the insulation channel 11 in order to be electrically insulated from the inner shaft 2. The insulation channel 11 is made of an electrically insulating material and electrically insulates the HF coil 12 and the electrical supply lines thereof from the inner shaft 2 and outer shaft 3. In order to ablate tissue, the insulation channel 11 at least slightly protrudes axially beyond the distal end of the inner shaft 2. Insulation channel 11 and HF coil 12 can be mounted rigidly relative to the inner shaft 2, although they can preferably also be axially adjusted with respect to the inner shaft 2 in order to transfer the HF coil 12 to a working position, as is explained in detail below.

According to FIG. 2, the HF coil 12 protrudes axially beyond the distal opening of the insulation channel 11 and has three sub-portions: a connection portion 15, a lateral ablation edge 16, and a symmetrically curved ablation edge 17.

According to FIG. 2, a symmetrically curved ablation edge 17 is formed at the distal end of the HF coil and is rounded in a laterally symmetrical manner. By virtue of this arrangement, an applied force can be concentrated in a small front region of the symmetrically curved ablation edge 17. In particular, the symmetrically curved ablation edge 17 can have a uniform symmetrical curvature. The ablation edge 17 in this case expediently extends perpendicularly with respect to the mid-line M, although according to other embodiments it can in principle also extend in a manner inclined at an acute angle to this mid-line M. The ablation edge 17 is adjoined laterally by a lateral ablation edge 16, which edges are connected by a connection portion 15 to supply lines that extend in the insulation channel 11 and serve to supply a high-frequency alternating current.

In the insertion position shown in FIG. 2, the HF coil 12, during the insertion of the distal end of the shaft 2, 3, preferably does not protrude radially beyond the outer profile of the outer shaft 3, such that the HF coil 12 cannot cause tissue damage in the insertion position. For this purpose, the HF coil 12 can also be retracted axially to the distal end of the shaft 2, 3 or can even be retracted completely into the interior of the hollow inner shaft 2.

As is explained below, the angle orientation of the HF coil 12 relative to the mid-line M can be adjusted in a controlled manner, such that it can be transferred to a working position in which the HF coil protrudes radially beyond the outer profile of the outer shaft 3. For this purpose, the connection portion 15 is made of a flexible or elastic, electrically conductive material, such that the angle orientation of the HF coil 12 relative to the mid-line M can be adjusted in a controlled manner by bending or kinking of the connection portion 15. The remaining portions of the HF electrode 10, for example the ablation edge 17, can altogether be less flexible or elastic than the connection portion 15, for example as a result of a greater material thickness of the electrical conductor in these remaining portions.

Figure 3A:
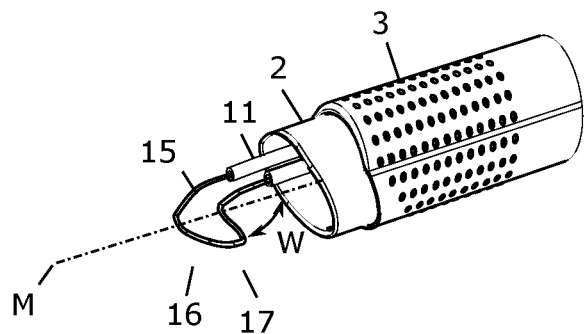
FIG. 3a shows a schematic perspective view of the distal region of the medical instrument according to FIG. 2 in an angled position or working position of the HF electrode.

FIG. 3a shows a detailed view of the distal portion 6 of the medical instrument 1 according to a first preferred embodiment. In this embodiment, the angle orientation of the HF coil relative to the mid-line M can be adjusted in a controlled manner by bending of the connection portion 15, as is indicated by the double arrow. In this way, the size of the angle W between the HF coil and the mid-line M can be modified.

For this purpose, the HF coil is prestressed, preferably elastically prestressed, to the working position shown in FIG. 3a, which can be readily achieved through suitable shaping and choice of material of the HF coil. By means of a pulling rod, which is coupled to the HF coil, it is now possible for the HF coil to be adjusted axially toward the distal end of the inner shaft 2. In this way, the insulation channel 11 finally comes into contact with the inner wall of the inner shaft 2 or with guide elements provided at the distal end of the inner shaft 2, as a result of which a bending back of the HF coil to the insertion position according to FIG. 2 is effected. This restoring of the HF coil from the working position to the rest position can take place continuously, i.e. the angle of inclination of the HF coil relative to the mid-line M decreases more and more the further the HF coil is moved back to the distal end of the inner shaft. According to a further embodiment, the material of the HF coil, at any rate in the region of the connection portion 15, can also induce a kind of bi-stable behavior, such that the angle of inclination of the HF coil relative to the mid-line M during the movement of the HF coil toward the distal end of the inner shaft 2 does not substantially change initially, but the HF coil finally snaps into the non-angled rest position according to FIG. 2 when a predetermined region is passed, or such that the angle of inclination of the HF coil relative to the mid-line M during the movement of the HF coil away from the distal end of the inner shaft 2, does not substantially change initially, but the HF coil finally snaps into the angled working position according to FIG. 3a when a predetermined region is passed.

For this purpose, the HF coil 12 or at least the connection portion 15 thereof can also be made of an (electrically conductive) memory metal, in particular an electrically conductive shape-memory alloy. In such a case, the angle of inclination of the HF coil relative to the mid-line can also be modified in a controlled manner by suitable modification of a current or preferably the temperature of the memory metal.

By moving the HF coil 12 into and out of the inner shaft 2, an angle W between the mid-line M and the HF coil 12 can be adjusted in a controlled manner.

Figure 3B:
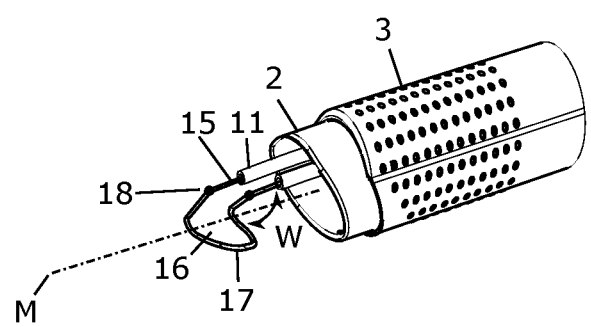
FIG. 3b shows a schematic perspective view of the distal region of the medical instrument according to a further embodiment of the present invention, with an HF coil whose angle position is adjustable in a controlled manner via hinges.

FIG. 3b shows the detailed view of the distal portion 6 of the medical instrument 1 according to a further embodiment, in which the angle orientation of the HF coil relative to the mid-line M can be adjusted in a controlled manner via hinges 18 provided in the region of the HF coil. The hinges 18 are expediently provided in the region of the connection portions 15 or in the transition region to the lateral ablation edge 16, as is shown in FIG. 3b. The angular mobility of the hinges 18 is expediently limited here to the desired angle range, which can be easily achieved by a configuration, for example, as rotary hinges with suitable angle stops. The HF coil can thus be adjusted to stop at a rest position in which the connection portion 15 extends parallel to the mid-line M and the HF coil preferably does not protrude beyond an inner profile formed by inner faces of the inner shaft 2 or beyond an outer profile formed by outer faces of the outer shaft 3. Moreover, the HF coil can be adjusted to stop at a suitable working position in which the HF coil is inclined at an acute angle relative to the mid-line M and protrudes radially beyond the outer profile of the outer shaft 3. For this purpose, the mechanical adjustment of the HF coil can be effected in particular by means of a pulling or pushing rod which is coupled to the HF coil.

Springs can be arranged at the hinges 18 in order to prestress the HF coil 12 elastically to the rest position or working position.

This embodiment is suitable in particular for a combination with a lever mechanism for controlled adjustment of the angle of inclination of the HF coil relative to the mid-line M, as is explained below, wherein in this case the springs can be configured to keep the connection portion 15 of the HF coil 12 straight.

Figure 3C:
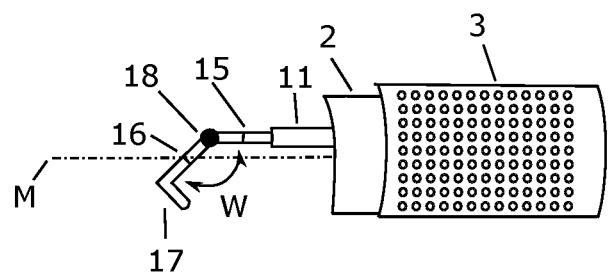
FIG. 3c shows a side view of the distal region according to FIG. 3b in an angled position of the HF coil.

FIG. 3c shows a side view of the distal region according to FIG. 3b in an angled working position of the HF coil, in which position the HF coil preferably protrudes radially beyond the outer profile of the outer shaft 3.

Figure 4:
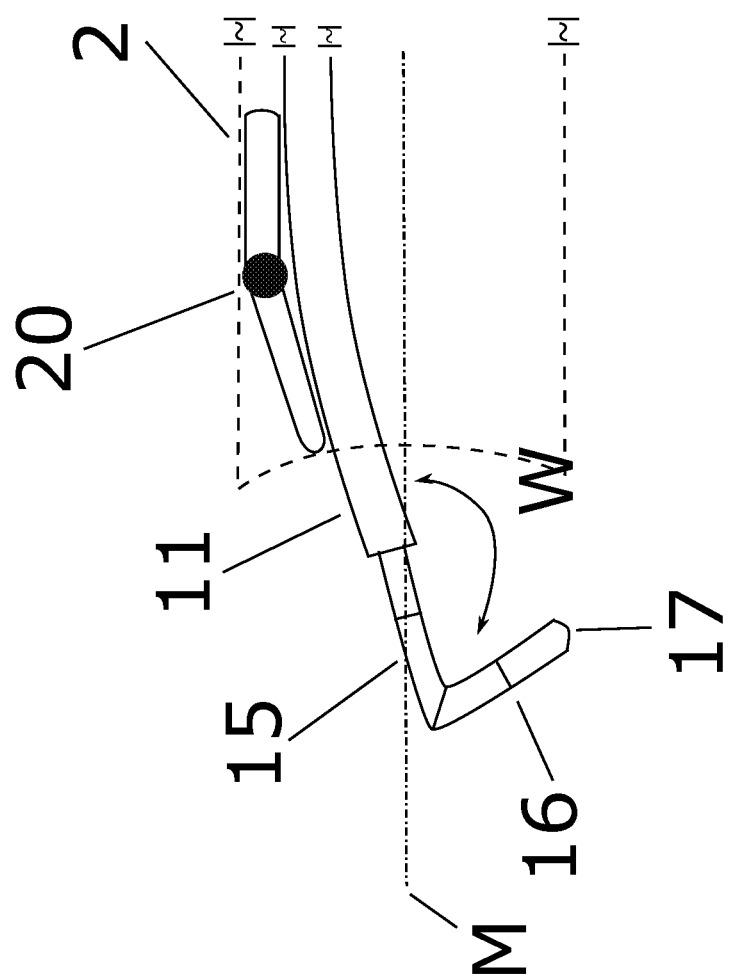
FIG. 4 shows a side view of the distal region of the medical instrument according to a further embodiment of the present invention, wherein the angle position of the HF electrode is adjustable by means of an angling lever.

FIG. 4 shows a side view of the distal portion 6 of the medical instrument 1 according to a further embodiment, wherein details of the inner shaft 2 have been omitted for reasons of simplification. In this embodiment, an additional angling lever 20 is arranged as angling element at the distal end of the hollow inner shaft 2. In this embodiment, the distal end of the angling lever 20 can be rotated about an axis until said angling lever finally comes to bear on the outer face of the insulation channel 11. By further modification of the angle position of the distal end of the angling lever 20, the insulation channel 11, together with the conductor portions of the HF electrode guided therein, is finally bent or kinked further, until finally a working position is reached which is shown in FIG. 4. Conversely, by restoring the angle position of the distal end of the angling lever 20, the distal end of the angling lever 20 can be released again from the outer face of the insulation channel 11, such that the insulation channel 11, together with the conductor portions of the HF electrode guided therein, can be adjusted back to a rest position. The angle position of the angling lever 20 can preferably be modified continuously, as a result of which a very fine variation of the angle orientation of the HF electrode relative to the mid-line M can be achieved. To control the angling lever 20, control wires or lines can be routed through the inner shaft 2 or outer shaft 3.

Instead of a mechanical angling lever 20, it is of course also possible for a piezoelectric element or a thermally adjustable element to be used as angling element.

Alternatively, the angling lever 20 can in principle also be configured in order to adjust only the angle orientation of the HF coil 12, namely by interaction only with electrically conductive portions of the HF coil, for example the elastic and flexible connection portion 15. In such a case, the angling lever 20 is made of an electrically insulating material, for example of a non-conductive plastic, or is rotatably mounted in a manner at least electrically insulated from the inner shaft 2. Or the inner shaft 2 is guided in an electrically insulated manner with respect to the outer shaft (not shown in FIG. 4).

According to a further embodiment, the angling element 20 can also be arranged in a fixed position and non-rotatably at the distal end of the inner shaft 2. Here, the HF electrode is mounted axially displaceably in the hollow inner shaft 2 and can be retracted sufficiently far into the inner shaft 2. When the HF electrode is moved axially out of the inner shaft 2, the HF electrode finally comes into contact with the angling element 20, the shape of which then effects a controlled angle adjustment of the HF electrode upon further deployment of the HF electrode from the inner shaft 2. As is shown schematically in FIG. 4, the angling element 20 can, for example, be arcuately curved, in the manner of an arcuately curved angling projection on the inner circumference of the hollow inner shaft 2, wherein the supply lines of the HF electrode on the inner face of the inner shaft 2 extend radially farther apart from the mid-line M than the geometric center of the angling element 20. Therefore, during the deployment of the HF electrode from the inner shaft 2, portions of the HF electrode first come into contact with the angling element 20. During the deployment of the HF electrode from the inner shaft 2, the HF electrode becomes increasingly bent or kinked, for example in the region of the connection portion 15 or of the hinges provided in this region.

FIG. 5a shows the detailed view of the distal portion 6 of the medical instrument 1 according to a further embodiment. In this embodiment, the insulation channel 11 or at least the distal end of the insulation channel 11 is made of a memory material, of which the rest position with respect to the mid-line M of the hollow inner shaft 2 is rectilinear or angled. By applying an electrical voltage, suitably changing the temperature or changing further physical parameters of the memory material, the insulation channel can be bent or can be transferred back to a rectilinear position, which accordingly also deforms the conductor portions of the HF electrode that are guided therein. In this way, the profile of the insulation channel can be modified and thus the angle orientation of the HF electrode relative to the mid-line M can, as desired, be adjusted in a controlled manner.

FIG. 5b shows the detailed view of the distal portion 6 of the medical instrument 1 according to a further embodiment. In this embodiment, the distal end of the inner shaft 2, which protrudes axially beyond the distal end of the outer shaft 3, is made of a memory material, of which the rest position with respect to the mid-line M of the hollow outer shaft 3 is rectilinear or angled. The supply lines of the HF electrode are expediently guided at a comparatively short distance from the inner surface of the inner shaft 2, such that even relatively small changes of shape of the inner shaft have the effect that the supply lines of the HF electrode come into contact with the inner face of the inner shaft 2 and the HF electrode is suitably adjusted upon further deformation of the memory material. By applying an electrical voltage, suitably changing the temperature or changing further physical parameters of the memory material, the angle orientation of the HF electrode relative to the mid-line M can thus, as desired, be adjusted in a controlled manner.

Alternatively, the inner shaft 2 can itself be configured as part of a pulling or pushing rod which, upon axial adjustment, effects a desired change of shape of the distal end of the inner shaft 2.

According to a further embodiment, the portions of the HF electrode that protrude axially beyond the distal end of the shaft can themselves be made directly of a memory metal, in particular of an electrically conductive shape-memory alloy, such that, by applying an electrical voltage, suitably changing the temperature or changing further physical parameters of the memory metal, the angle orientation of the HF electrode relative to the mid-line can be suitably adjusted.

Overall, according to the above embodiments, a controlled adjustment of the angle orientation of the HF electrode relative to the mid-line can be achieved. In combination with an axial adjustment of the medical instrument, it is thus possible according to the invention to achieve practically any desired positioning of the HF electrode, even at positions remote from the mid-line, in order to perform specific tissue ablation there. Limitations of conventional medical instruments, which limitations were caused in particular by the comparatively rigid material of conductor portions of the HF electrode, can be overcome by the configuration according to the invention.

As is shown by way of example in FIG. 5, a new work axis A is formed by the HF coil in the bent or kinked working position, which work axis A is inclined at an acute angle W relative to the mid-line M. According to a preferred use in transurethral resection, the medical instrument is configured as a resectoscope which, in an insertion position of the HF electrode, is inserted through the urinary canal into the operating region. The HF electrode, given a suitable axial position, is then brought to a working position with a suitable angle of inclination W of the work axis A relative to the mid-line M, as is shown in FIG. 5b. This can also bring about an axial adjustment of the HF electrode. In the working position, as will be readily apparent to a person skilled in the art, by suitable longitudinal adjustment of the shaft or of the HF electrode, a position can always be found in which the distal end of the HF electrode sufficiently reaches or touches tissue portions that are to be ablated in the region of the bladder neck. By axial adjustment of the shaft or the HF electrode axially along the aforementioned insertion axis and/or by changing the angle of inclination of the HF electrode relative to the shaft or the insertion axis, it is thus possible gradually to reach practically any desired regions in the operating region laterally with respect to the insertion axis. As can be readily seen from FIG. 6, this also applies correspondingly to tissue portions in the region of the prostate, which are located laterally with respect to the aforementioned insertion axis. The reach of the resectoscope according to the invention is basically limited only by the size of the angle adjustment of the HF electrode and the distance by which the distal end of the HF electrode can protrude radially beyond the outer profile of the shaft.

LIST OF REFERENCE SIGNS 1 medical instrument
2 inner shaft
3 outer shaft
4 positioning handle
5 operating handle
6 distal end
10 HF electrode
11 insulation channel (for electrical insulation)
12 HF coil
15 connection portion
16 lateral ablation edge
17 symmetrically curved ablation edge
18 hinge
20 angling lever
100 bladder
101 orifice of the ureter
102 region of the inner sphincter muscle
103 region of the outer sphincter muscle
104 region of the prostate
105 mucosa
106 trigonum vesicae
107 bladder neck
110 shaft
111 HF electrode
M mid-line (of the shaft)
W angle
A work surface mid-line

We claim:

1. Medical instrument for minimally invasive tissue ablation by means of an HF electrode, with a hollow shaft having a mid-line (M), wherein;
   the HF electrode is electrically insulated from the hollow shaft, is arranged at a distal end of the hollow shaft and, in order to ablate tissue, protrudes axially beyond the hollow shaft at least in part;
   wherein the distal end of the HF electrode is formed by a lateral ablation edge which merges, via symmetrically curved ablation edge, into a connection portion;
   an angle orientation of the HF electrode relative to the hollow shaft is adjustable in a controlled manner to a fully extended working position in which the HF electrode protrudes radially beyond an outer circumference of the hollow shaft in order to ablate tissue;
   wherein the lateral ablation edge intersects the mid-line (M) in the working position; and
   during an axial adjustment of the connection portion of the HF electrode in the working position, the angle orientation of the curved ablation edge of the HF electrode is modified.

2. Medical instrument according to claim 1, wherein the HF electrode has an electrical insulation channel and an HF coil, wherein
   the insulation channel electrically insulates the HF electrode from the hollow shaft and protrudes axially beyond a distal end of the shaft, and
   a distal end of the HF coil protrudes axially beyond the distal end of the insulation channel in order to ablate tissue.

3. Medical instrument according to claim 2, wherein the angle orientation of the connection portion relative to the mid-line (M) of the hollow shaft is adjustable in a controlled manner in order to adjust in a controlled manner the angle orientation of the HF coil relative to the hollow shaft.

4. Medical instrument according to claim 3, wherein the connection portion is made of a flexible or elastic, electrically conductive material, and the angle orientation of the HF coil relative to the hollow shaft is adjustable in a controlled manner by bending or kinking of the connection portion.

5. Medical instrument according to claim 4, wherein the HF electrode is elastically prestressed to the working position, in which a distal end of the connection portion is bent or kinked relative to a proximal end of the connection portion in order to enclose an acute angle with a mid-line (M) of the hollow shaft.

6. Medical instrument according to claim 1, further comprising an adjustable angling element, wherein the angle orientation of the HF electrode relative to the hollow shaft is adjustable in a controlled manner by adjustment of the angling element in contact with a portion of the HF electrode or of the electrical insulation channel.

7. Medical instrument according to claim 6, wherein the angling element is a piezoelectric element, or a thermally adjustable element, or a mechanically adjustable element.

8. Medical instrument according to claim 3, wherein the HF electrode has hinges which are arranged on the connection portion, such that the angle orientation of the HF coil relative to the hollow shaft is adjustable in a controlled manner by adjustment of the hinges.

9. Medical instrument according to claim 8, further comprising a pulling or pushing rod which is coupled to the HF coil such that an adjustment of the pulling or pushing rod causes an adjustment of the angle orientation of the HF coil relative to the hollow shaft.

10. Medical instrument according to claim 8, wherein elastic restoring means are assigned to the hinges in order to elastically prestress the HF coil to a rectilinear or angled rest position.

11. Medical instrument according to claim 1, wherein the HF electrode is formed at least in part from a memory metal, which is configured such that the angle orientation of the HF electrode relative to the hollow shaft is adjustable in a controlled manner, in particular by application of an electric current or by a temperature change.

12. Medical instrument according to claim 1, wherein the hollow shaft has a hollow outer shaft and an inner shaft received therein, wherein the inner shaft is guided longitudinally displaceably in the hollow outer shaft, and wherein the HF electrode can be retracted completely into the hollow outer shaft.

13. Medical instrument according to claim 1, wherein an angle of inclination of the HF electrode relative to a mid-line (M) of the hollow shaft is adjustable by up to 90°.

14. Medical instrument according to claim 1, wherein the lateral ablation edge comprises a first material, wherein the connection portion comprises a second material, and wherein the first material is less flexible than the second material.

* * * * *